US00PP08860P

United States Patent [19]

Schumann

[11] Patent Number: Plant 8,860

[45] Date of Patent: Aug. 9, 1994

[54] GERANIUM PLANT NAMED FISTIFFY

[75] Inventor: Ingeborg Schumann, Albstadt, Fed. Rep. of Germany

[73] Assignee: Florfis AG, Binningen, Switzerland

[21] Appl. No.: 94,329

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fistiffy, particularly characterized by the combined features of semi-double round flower form, purple pink flower color with red and white markings, medium green foliage with very slight zonation, and low, compact plant habit.

1 Drawing Sheet

The present invention comprises a new and distinct cultivar of geranium, botanically known as *Pelargonium zonale l'hert,* and hereinafter referred to by the cultivar name Fistiffy.

Fistiffy is a product of planned breeding program which had the objective of creating new geranium cultivars with violet pink flowers with distinct markings, good cultivation characteristics, and a plant habit which is not too compact.

Fistiffy was originated from a self pollination hybridization made by the inventor Ingebore Schumann in a controlled breeding program in Galdar, Gran Carania, Spain in 1982. The parent was an inbred seedling derived by selfing the unpatented cultivar Rospen. Rospen is characterized by bluish pink flowers with red and white markings on the upper petals, light to medium green foliage with zonation (not always very distinct), and compact plant habit. Fistiffy is a chance seedling of this inbred seedling. Rospen comparatively often has spontaneous seed set, and as there are no characteristics that would give hints to interbreeding from different varieties, Fistiffy is with high certainty an inbred seedling (2nd generation) from Rospen.

Fistiffy was discovered and selected as one flowering plant within the progeny of the stated cross by Ingeborg Schumann in 1986 in a controlled environment in Galdar, Gran Canaria, Spain.

The first act of asexual reproduction of Fistiffy was accomplished when vegetative cuttings were taken from the initial selection in 1991 in a controlled environment in Galdar, Gran Canaria, Spain.

Horticultural examination of plants grown from these cuttings initiated in May 1989 in Hillscheid, Federal Republic of Germany, and continuing thereafter, has demonstrated that the combination of characteristics as herein disclosed for Fistiffy are firmly fixed and are retained through successive generations of asexual reproduction.

Fistiffy has not been observed under all possible environmental conditions. The phenotype may vary significantly with variations in environment such as temperature, light intensity and day length without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristic of Fistiffy, which in combination distinguish this geranium as a new and distinct cultivar:

1. Purple pink flower color
2. Semi-double round flower type
3. Red and white markings on upper and lower petals
4. Medium green foliage with medium zonation
5. Compact growth habit
6. Medium spring flower response
7. Large Umbels Of the many commercial cultivars known to the present inventor, the most similar in comparison to Fistiffy is Rospen.

Reference is made to attached Chart A which compares certain characteristics of Fistiffy to those same characteristics of Rospen.

In general comparison to Rospen, Fistiffy has superior flowers. The flower color of Fistiffy is somewhat more intense, the flower form is nearly round as opposed to the zygomorph form of Rospen, and the flowers of Rospen are never quite open. The round flower form has the effect that markings on the lower petals are almost as distinct as that on the upper petals.

The accompanying color photograph drawing shows typical flower and foliage characteristics of Fistiffy, with colors being as true as possible with illustrations of this type.

In the following description color references are made to The Royal Horticultural Society Color Chart. The color values were determined indoors from plants grown in the greenhouse in May at Hillscheid, Federal Republic of Germany.

Classification:

*Botanical.*—A hybrid of the species *Pelargonium zonale l'Hert.*

*Commercial.*—Zonal geranium, cv., Fistiffy.

INFLORESCENCE

A. Umbel:

*Shape.*—Semi-spherical.

*Average diameter.*—110 mm.

*Average depth.*—60 mm.

*Peduncle length.*—160 mm.

*Pedicel length.*—31 mm.

*Pedicel color.*—Light red.

*Number of flowers per umbel.*—40–50.

B. Corolla:

*Average diameter.*—47 mm.

*Form.*—Semi-double.

*Average number of petals.*—6–9.

*Average number of petaloids.*—0–2.

*Color (general tonality from a distance of three meters).*—Purple pink.

*Color of upper petals.*—67 B.

*Color of lower petals.*—67 B

*Markings of upper petals (weaker on lower petals)*—.—Purple eye (57A) and white base.

*Color of lower surface of petals.*—71 D and lighter.

*Color of sepals.*—Partly anthocyanine colored.

*Number of sepals.*—5.

C. Bud:

*Shape.*—Elliptic.

*Color (adaxial).*—Green, with little anthocyanin at the base.

*Color (abaxial).*—Rose red.

D. Reproductive organs:

*Androecium.*—7–9 fertile anthers, orange pollen.

*Gynoecium.*—5–6 lobed stigma, red style and stigma.

E. Spring flowering response period: In Hillscheid, Federal Republic of Germany, in 1993 plants had on average 1.0 flowers opened 10 weeks after planting of unrooted cuttings.

F. Outdoor flower production: The flower count in 1992 in Hillscheid, Federal Republic of Germany was between 30 and 35 flowers per plant for May through August observation period.

G. Durability: Average.

PLANT

A. Foliage:

*Form.*—Kidney-shaped.

*Margin.*—Bicrenate.

*Size of leaf.*—About 10 cm.

*Color of upper surface.*—Medium green, approximately 137D.

*Color of zonaation.*—Darker green, approximately 147A.

*Tolerance of botrytis.*—Average.

B. General appearance and form:

*Internode length.*—10–15 mm.

*Branching pattern.*—2.3 branches per week.

*Height (12 week old plants).*—12 cm. ,0070

I claim:

1. A new and distinct cultivar of geranium plant named Fistiffy, as illustrated and described.

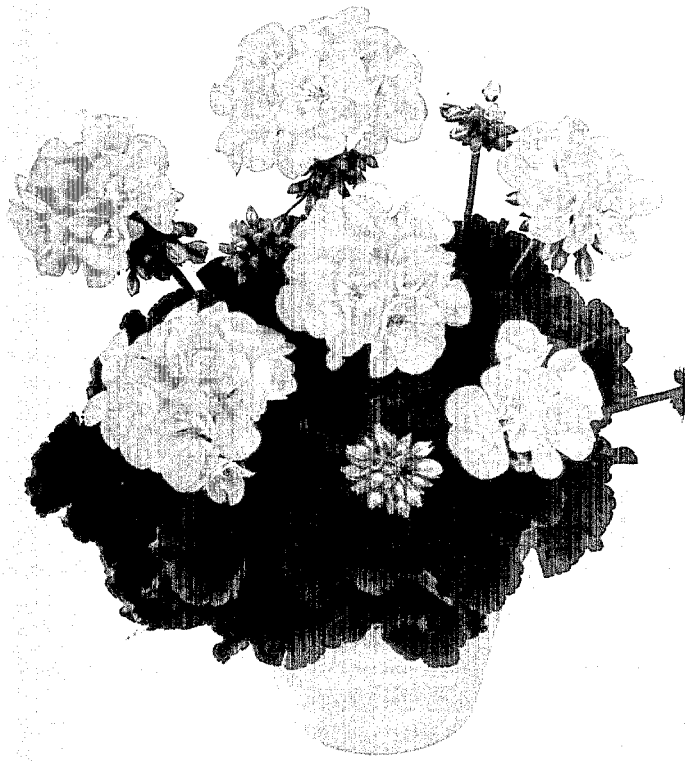

* * * * *